United States Patent [19]

Rogachev et al.

[11] 4,060,760
[45] Nov. 29, 1977

[54] EDDY CURRENT SENSOR FOR NON-DESTRUCTIVE TESTING THE QUALITY OF ELECTRICALLY CONDUCTIVE THROUGH-HOLE PLATING IN PRINTED CIRCUIT BOARDS

[76] Inventors: Viktor Igorevich Rogachev, Jurievsky pereulok, 22, korpus 2, kv. 55; Vasily Vasilievich Sukhorukov, 2 Vladimirskaya, 50, korpus 2, kv. 51; Petr Nikolaevich Shkatov, Lefortovsky val, 7/6, korpus 4, kv. 69, all of Moscow, U.S.S.R.

[21] Appl. No.: 656,082

[22] Filed: Feb. 6, 1976

[30] Foreign Application Priority Data

Feb. 11, 1975 U.S.S.R. .................................. 2100851

[51] Int. Cl.² ........................................... G01R 33/12
[52] U.S. Cl. .................................... 324/2.9; 209/81 R
[58] Field of Search ........... 324/37, 40, 34 MC, 34 R; 209/81 R, 81 A

[56] References Cited

U.S. PATENT DOCUMENTS

| 2,985,300 | 5/1961 | Boehm et al. | 209/81 R |
| 3,718,855 | 2/1973 | Rogel et al. | 324/37 |
| 3,825,822 | 7/1974 | Forster | 324/40 |
| 3,840,802 | 10/1974 | Anthony | 324/40 |

*Primary Examiner* — Robert J. Corcoran

[57] ABSTRACT

An eddy current sensor for non-destructive testing the quality of electrically conductive through-hole plating in printed circuit boards in which a magnetic probe member is provided with a device for moving the probe enveloping its exciting winding and two opposing measuring windings which are magnetically coupled with the exciting winding. These exciting and two opposing measuring windings are rigidly connected so that the exciting winding is positioned between the measuring windings with gaps provided to insert a printed circuit board to be tested. The magnetic probe member is inserted into the hole with the help of the device for moving the probe.

5 Claims, 6 Drawing Figures

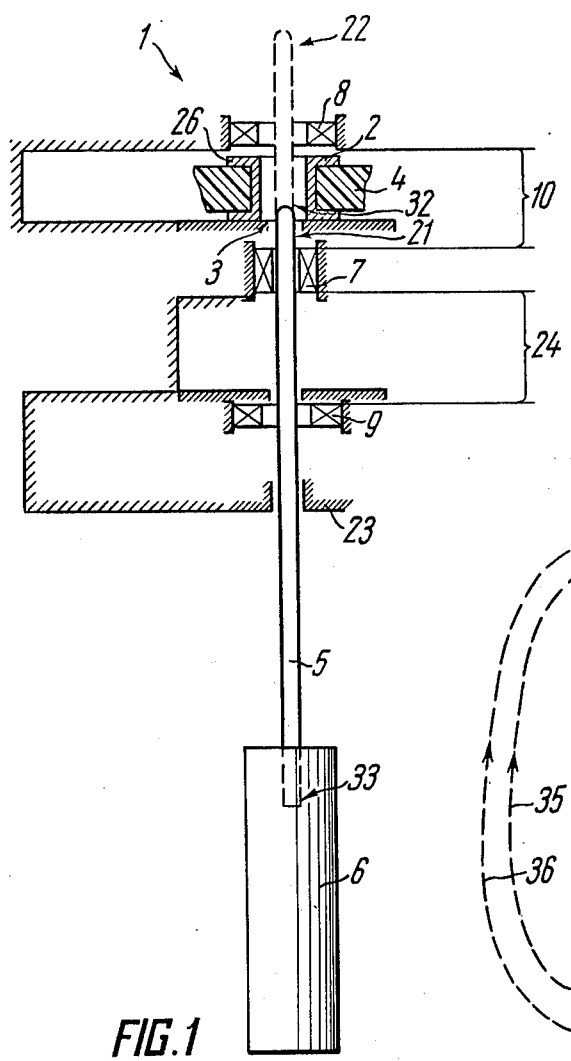
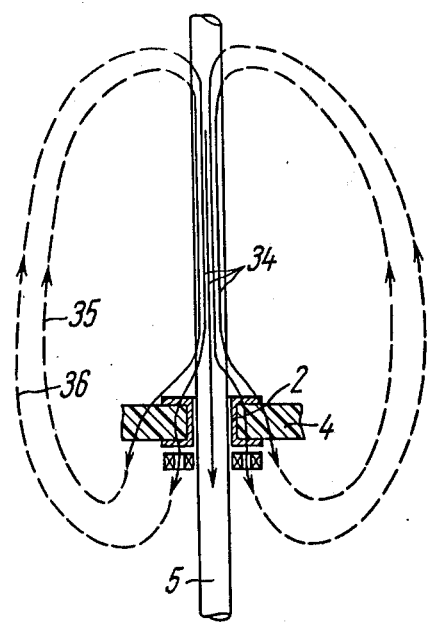
FIG.1
FIG.6

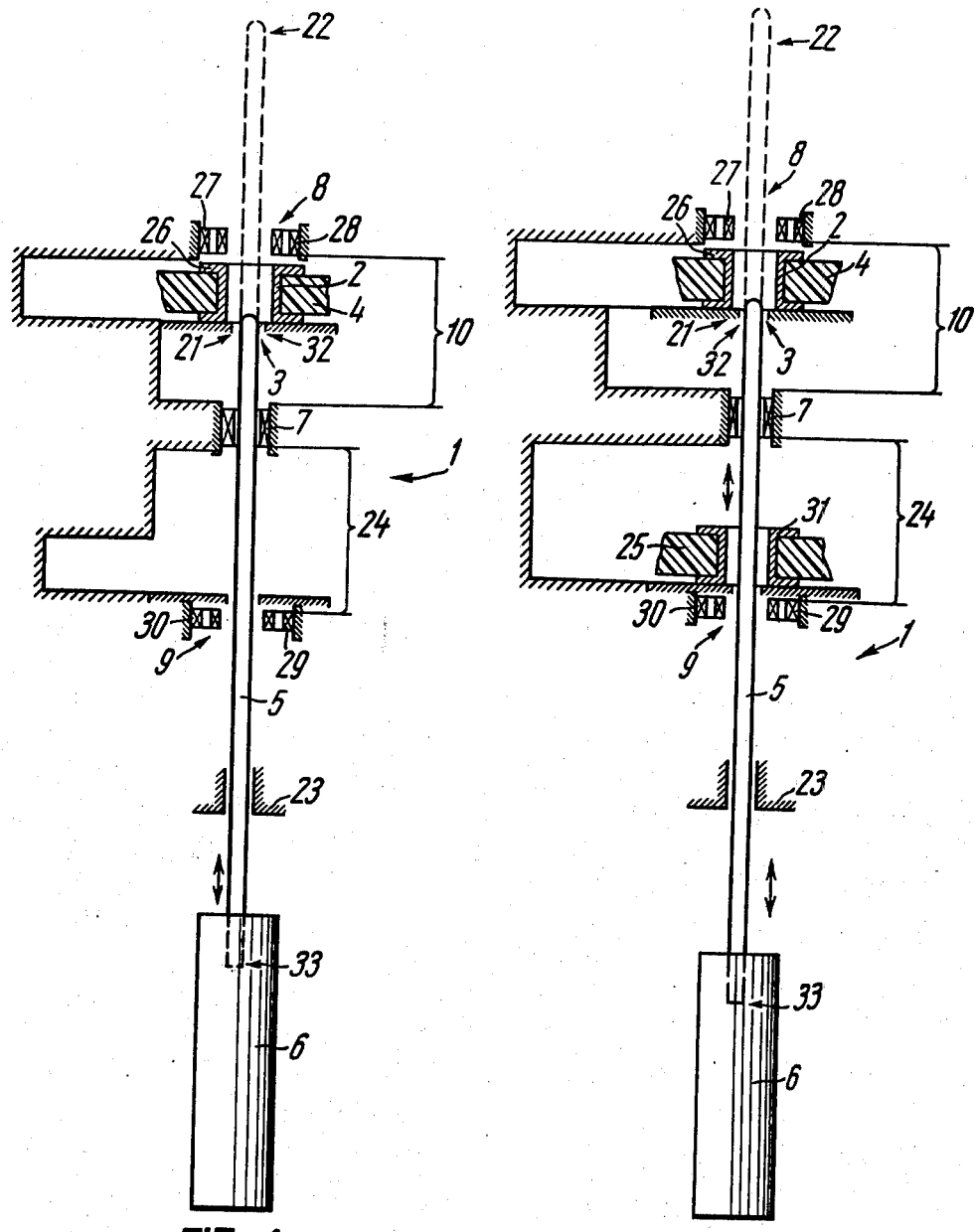

EDDY CURRENT SENSOR FOR NON-DESTRUCTIVE TESTING THE QUALITY OF ELECTRICALLY CONDUCTIVE THROUGH-HOLE PLATING IN PRINTED CIRCUIT BOARDS

BACKGROUND OF THE INVENTION

This invention relates to the field of devices for non-destructively testing electrically conductive materials and, in particular, to an eddy current sensor for non-destructive testing of the quality of electrically conductive through-hole plating in printed circuit boards.

The invention can be employed in machine building industry, instrument making, computer technology and electronics to test the quality of electrically conductive hole wall platings, inner tube surfaces, electrically conductive through-hole plating in printed circuit boards and other hollow objects with electrically conductive inner surface.

There is known a mutual-inductance coupling probe device for testing the integrity of through-hole plating in printed circuit boards (cf. U.S. Pat. No. 3,840,802, Cl.224–37, filed 1974). This sensor comprises two magnetic structures which are separated by electrically conductive shields. The magnetic circuits are provided with windings and are made so that their pole faces are turned towards the wall of the tested hole and located at an angle of 90° apart. The winding of one of the magnetic circuits serves to excite an alternating magnetic flux in the wall of the tested hole, whereas EMF is induced in the winding of the second magnetic circuit which depends on eddy currents in the hole wall plating and, consequently, on the quality of this wall plating (thickness of the electrically conductive plating, its specific conductivity, various defects).

The sensitivity of the known sensor in measuring the thickness of an electrically conductive plating is low, as well as its testing output capacity, and the manufacturing process is rather complicated. Low accuracy of measurements derives from the fact that the EMF of the measuring winding is to a substantial degree a function of the distance between the butt ends of the magnetic circuits and the walls of a tested hole. That is why considerable errors are introduced by radial motions of the sensor within the hole.

Poor output capacity of testing can be accounted for by the fact that the sensor probe is to be very accurately located within the hole with the electrically conductive plating-to-be-tested and then moved along the plated wall.

Since the holes in printed circuit boards have diameters of the order of 0.5–2 mm, manufacturing of a probe device containing electrically conductive shields and intricately shaped magnetic circuits of strict sizes becomes a hard task to cope with.

There is also known an eddy current sensor for non-destructive testing of the quality of electrically conductive through-hole plating in hollow objects.

This eddy current sensor comprises an exciting and two opposing measuring windings which can slide along a magnetic circuit rod. This permits increase of the voltage balance level of the measuring windings before measurements by changing the distance between the exciting and measuring windings. When the maximum possible level of voltage balance of the measuring windings is attained by shifting the windings, they should be fixed on the magnetic circuit rod.

When alternating current is run through the exciting winding, an alternating magnetic field is produced. Its lines of force propagate along the magnetic circuit axis and close in the air. Then the mutual coupling between corresponding measuring and exciting windings depends upon the distance therebetween. By moving windings in relation to each other, a high degree of voltage balance can be attained in measuring windings. In case the magnetic circuit is placed in the hole space or at its entrance, eddy currents are induced in the electrically conductive plating which redistribute the flux between the main magnetic flux in the rod and the leakage flux.

The known sensor accuracy is low, as well as its output capacity for testing electrically conductive plating in holes of printed circuit boards.

The above described sensor may be used for testing the quality of electrically conductive through-hole plating in printed circuit boards as follows. If a tested printed circuit board is placed between the exciting and measuring windings, miniature measuring windings should be manufactured with a diameter less than the diameter of the tested hole. This makes the process of manufacturing an eddy current sensor complicated, and reduces its reliablility and testing output capacity. It is also possible that the tested printed board is placed at the tip of the magnetic circuit or that the magnetic circuit with windings secured thereon is introduced into the tested hole so that a corresponding measuring winding is at the moment of measurement between the exciting winding and the tested printed circuit board. When the measuring windings and the magnetic circuit are positioned in relation to the hole in this way, the signal of the eddy current sensor is highly dependent on the distance between the corresponding winding and the test object. Besides, axial movement of the measuring sensor with windings in relation to the test object is required before measurements followed by its fixation, which also reduces the testing output capacity.

The object of the present invention is to increase the accuracy of testing the quality of electrically conductive through-hole plating in printed circuit boards.

SUMMARY OF THE INVENTION

This object is achieved by providing an eddy current sensor for non-destructive testing the quality of electrically conductive through-hole plating in printed circuit boards comprising a magnetic probe member, an enveloping exciting winding and two opposing measuring windings magnetically coupled with the exciting winding. The magnetic probe member is, according to the invention, provided with a device for moving the probe, whereas the exciting and two opposing measuring windings are rigidly connected to each other so that the exciting winding is placed between the measuring windings with gaps provided for insertion of a tested printed circuit board, into which hole the magnetic probe member is put with the help of the device for moving the probe.

It is advisable that to increase the testing capacity the device for moving the probe of the magnetic probe member of the eddy current sensor for non-destructive testing the quality of electrically conductive through-hole plating in printed circuit boards, is made as an electromagnetic drive.

It is also desirable that the electromagnetic drive comprises a solenoid, a magnetized screw coaxially positioned with a spring placed thereon and a ferromagnetic core connected by one of its ends to the spring and by the other end via a dielectric rod to the magnetic probe and able to move along the solenoid axis.

It is quite expedient that, to increase the "useful signal/interference" ratio of the eddy current sensor for non-destructive testing the quality of electrically conductive through-hole plating in printed circuit boards featuring termination pads, each of the measuring windings comprises sections being in aiding connection and positioned at a certain distance from the magnetic probe member and symmetrical about its axis, their projections being within the limits of corresponding termination pads of the hole of the tested printed circuit board.

It is also advisable that, to increase the degree of EMF balance of the measuring windings of an eddy current sensor for non-destructive testing the quality of electrically conductive through-hole plating in printed circuit boards the distance between the exciting and measuring windings constitutes more than 4–5 radii of the exciting winding, whereas the distance between the ends of the magnetic probe member to the measuring windings is more than 10 radii of the magnetic probe member.

The above-described eddy current sensor for non-destructive testing the quality of electrically conductive through-hole plating in printed circuit boards has a higher degree of testing accuracy. This is accounted for by the fact that the magnetic probe member can be moved by means of a drive and permits placing the tested printed circuit board between the exciting and one of the measuring windings. When a test object is positioned in such a way, the probe becomes much less sensitive to axial shifts of its windings in relation to the test object in the probes of measurements, whereas it becomes much more sensitive to parameters of electrically conductive through-hole plating in printed circuit boards. Besides, when switching from testing the quality of electrically conductive plating in one hole of a printed circuit board to testing the quality of electrically conductive plating in another hole of the printed circuit board, it is the magnetic probe member of the eddy current sensor that is being moved, since it has the operating and initial positions, which permits increase of the test output capacity of testing the quality of electrically conductive plating.

Another advantage of the above-described eddy current sensor consists in a higher "useful signal/interference" ratio with various changes in the parameters of terminal pads of holes in printed circuit boards. This is explained by the fact that the effect of the termination pads parameters --on the magnitude of the magnetic flux crossing the measuringwindings composed of sections being in aiding connection and positioned somewhat apart from the magnetic probe member and symmetrical to its axis (their projections being within the limits of corresponding termination pads of the hole in the printed circuit board)--is much less than the effect of varied parameters of electrically conductive through-hole plating in the printed circuit board upon the magnitude of said flux.

These and other objects and advantages of the invention will become apparent from the following description taken in conjunction with the accompanying drawings in which:

BRIEF DESCRIPTION OF THE DRAWINGS

FIG. 1 is a general view of an eddy current sensor for non-destructive testing the quality of electrically conductive through-hole plating in printed circuit boards, with a printed circuit board to be tested being inserted between exciting and measuring windings, according to the invention;

FIG. 4 is a general view of another embodiment of an eddy current sensor for non-destructive testing the quality of electrically conductive through-hole plating in printed circuit boards with a printed circuit board to be tested placed between the exciting and measuring windings, according to the invention;

FIG. 5 is a general view of another embodiment of an eddy current sensor with a test and sample printed boards placed between the exciting and measuring windings, according to the invention;

FIG. 6 is a schematic view of distribution of the magnetic field of the eddy current sensor in the vicinity of the test hole of a printed circuit board with an electrically conductive plating, according to the invention.

DESCRIPTION OF THE PREFERRED EMBODIMENTS

Figures 2, 3:
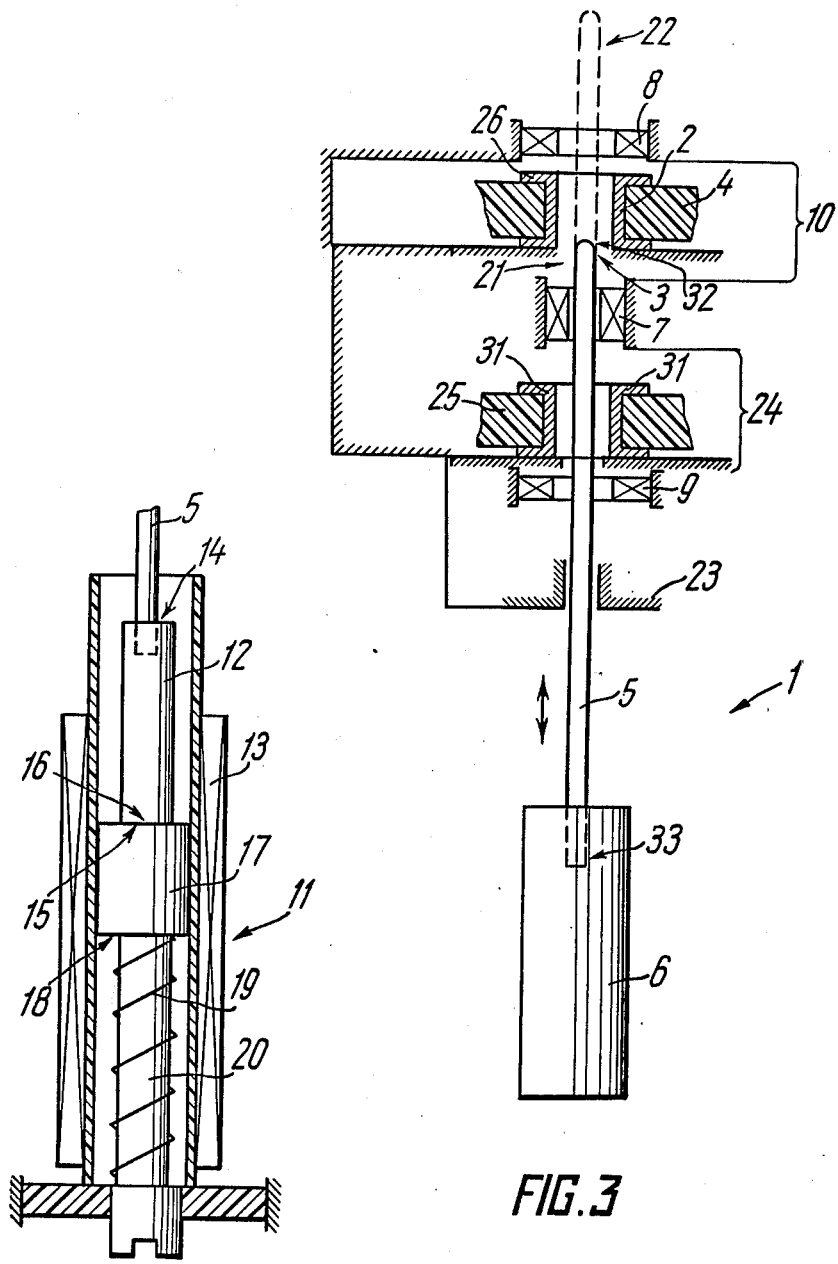
FIG. 2 is a general view of a device for moving the probe, made as an electromagnetic drive, according to the invention.
FIG. 3 is a general view of an eddy current sensor for non-destructive testing the quality of electrically conductive through-hole plating in printed circuit boards with a tested and a sample printed circuit boards inserted between the exciting and measuring windings, according to the invention.

An eddy current sensor 1 for non-destructive testing the quality of electrically conductive through-hole plating in printed circuit boards is shown in FIG. 1.

An eddy current sensor 1 for non-destructive testing the quality of an electrically conductive plating 2 within holes 3 of a printed circuit board 4 comprises a magnetic probe member 5 featuring a device for moving the probe 6. This makes it possible to move the magnetic probe member 5 in the hole 3 of the printed circuit board 4. The eddy current sensor 1 also comprises an exciting winding 7 inducing eddy currents in the electrically conductive plating 2 in the hole 3 of the printed circuit board 4. Two opposing measuring windings 8 and 9, which are magnetically coupled with the exciting winding 7, are situated at a certain distance from this exciting winding 7. The exciting winding 7 and the measuring windings 8 and 9 are rigidly connected to each other so that the exciting winding 7 is placed between the windings 8 and 9. There is a gap 10 between the exciting winding 7 and the measuring winding 8 to insert the test printed circuit board 4, into which hole 3 the magnetic probe member is put.

The travel means 6 (FIG. 2) of the magnetic probe member 5 is made as an electromagnetic drive 11.

The travel means 6 can be also as a mechanical, pneumatic or hydraulic drive.

But it is advisable to make the drive 11 electromagnetic, since the sensor 1 for testing the quality of the electrically conductive plating 2 provided with the electromagnetic drive 11 has higher output testing capacity and permits easier automation of the testing process.

The electromagnetic drive 11 comprises a non-ferromagnetic dielectric rod 12 placed coaxially in a solenoid 13. The dielectric rod 12 is connected by one of its ends 14 to the magnetic probe member 5 and by the other end 15 to a tip 16 of a ferromagnetic core 17 of the solenoid 13. The second tip 18 of the ferromagnetic core 17 is connected to a return spring 19 fit on a premagnetized screw 20 made of retentive material. The screw 20 serves as a support of the ferromagnetic core 17 in an initial position 21 of the magnetic probe member 4 shown in FIG. 1.

In an operating position 22 the magnetic probe member 5 is fixed with the help of a stop 23 limiting movements of the dielectric rod 12 along the axis of the magnetic probe member 5.

The quality of the electrically conductive plating 2 in holes 3 of the printed circuit board 4 can be also done with the use of a sample printed circuit board.

This permits determination by the results of measurements of deviations of the parameters of the electrically conductive plating 2 from the rated ones. It also permits simple calibration of the device with the proposed eddy current sensor 1, when the rated thickness of terminal pads of the tested hole 3 changes.

In this case a sample printed circuit board 25 is inserted into a gap 24 (FIG. 3) between the exciting winding 7 and the measuring winding 9. FIGS. 1 and 3 demonstrate embodiments of the eddy current sensor 1 with the measuring windings 8 and 9 enveloping the magnetic probe member 5, which may be expedient, if parameters of termination pads 26 of the test hole 3 vary insignificantly or if there are no terminal pads at all.

In case the thickness of the termination pads 26 of the hole 3 of the tested printed circuit board 4 is substantial and parameters of the termination pads 26 vary to a considerable degree, it is more wise to employ another embodiment of the eddy current sensor 1 for non-destructive testing the quality of electrically conductive plating 2, in the holes 3 of the printed circuit boards 4 illustrated in FIG. 4.

In this case the measuring windings 8 and 9 are made of sections. The measuring winding 8 consists of sections 27 and 28 being in aiding connection, whereas the measuring winding 9 consists of like sections 29 and 30 also being in aiding connection.

The sections 27 and 28 of the measuring winding 8 and the sections 29 and 30 of the measuring winding 9 are positioned at a certain distance from the magnetic probe member 5 and symmetrical about its axis. Projections of the sections 27 and 28, 29 and 30 lie within the limits of corresponding termination pads 26 of the hole 3 of the test printed circuit board 4.

Such construction of the measuring windings 8 and 9 permits increase of the "useful signal/interference" ratio, when parameters of the termination pads 26 of the test hole 3 vary.

This embodiment of the eddy current sensor 1 can be also employed to test the quality of the electrically conductive plating 2 in the hole 3 of the printed circuit board 4 through the use of a sample printed circuit board, which permits comparison of parameters, of the electrically conductive plating 3 in the hole 2 of the test printed circuit board 4, with corresponding parameters of the sample printed circuit board 25. In this case the sample printed circuit board 25 provided with termination pads 31 is inserted into the gap 24 (FIG. 5) between the exciting winding 7 and the measuring winding 9.

In this embodiment of the eddy current sensor 1 (FIG. 4) the distance between the exciting winding 7 and the measuring windings 8 and 9 exceeds 4–5 radii of the exciting winding 7, whereas the distance from the measuring windings 7 and 9 to the tips 32 and 33 of the magnetic probe member 5 exceeds 10 radii of said magnetic probe member 5.

This permits decrease of the interferences brought up by possible variations of the distance between corresponding measuring windings 8 and 9 and the tips 32 and 33 of the magnetic probe member 5 and the exciting winding 7.

The eddy current sensor for non-destructive testing the quality of electrically conductive through-hole plating in printed circuit boards operates as follows:

Prior to the process of testing the quality of the electrically conductive plating 2 (FIG. 1) in the plated-through holes 3 of the printed circuit boards 4, the magnetic probe member 5 of the eddy current sensor 1 is in the initial position 21. In this position the ferromagnetic core 17 (FIG. 2) is held by the magnetic field of the solenoid 13 and fixed by the magnetic forces of the screw 20.

When the test printed circuit board 4 is inserted into the gap 10 (FIG. 1), the current in the solenoid 13 (FIG. 2) is cut off and the magnetic probe member 5 is forced by the return spring 19 to the operating position 22 symmetrical in relation to the exciting winding 7, since the magnetic probe member is connected by its end 14 of the non-ferromagnetic dielectric rod 12 to the ferromagnetic core 17. The operating position 22 is fixed by the stop 23. Alternating current flowing through the exciting winding 7 (FIG. 1) induces a magnetic flux propagating along the magnetic probe member 5. This excites circular eddy currents in the test plating 2. As a result the magnetic flux propagating along the magnetic probe member 5 is displaced and increase the leakage flux. Information on the parameters of the electrically conductive plating 2 in the hole 3 of the test printed circuit board 4 can be obtained by measuring the difference between fluxes passing through the measuring windings 8 and 9 enveloping the magnetic probe member 5.

The sample printed circuit board 25 (FIG. 3) may be inserted into the gap 24. In this case the difference between the electrical voltages of the windings 8 and 9 is proportional to the deviation in plating parameters in the hole 3 from the sample parameters. Since the induced eddy currents are basically circular, they are circulating not only in the electrically conductive plating but in the termination pads 26 and 31 of the test printed circuit board 4 and the sample printed circuit board 25, respectively. The thickness of the termination pads 26 determines the sensitivity of the sensor 1 to the parameters of the electrically conductive plating 2. That is why a printed circuit board with nominal parameters of the termination pads 31 and devoid of the electrically conductive through-hole plating is convenient to be employed as the asmple printed circuit board 25.

In this case, prior to testing the parameters of the electrically conductive plating 2, such sample printed circuit board 25 is used to find out the sensitivity of a device featuring the eddy current sensor 1, whereas the signal of the sensor is proportional to the parameters of the electrically conductive plating 2, e.g., to the absolute value of the electrically conductive plating 2. Since the eddy currents are circular, the sensor 1 is sensitive to longitudinal cracks. If parameters of the termination pads 26 vary considerably within a batch of tested printed circuit boards or even in one such board, it may cause difficulties involving adjustment of the sensitivity of a device featuring the eddy current sensor 1. In this case, to increase the "useful signal/interference" ratio measurements of the leakage flux, variations are preferably done with the help of the measuring winding 8 (FIG. 4) comprising the sections 27 and 28 positioned under the termination pad 26 and symmetrical about the magnetic probe member 5 placed between the sections 29 and 30.

The measuring winding 9 is intended to compensate the voltage of the measuring winding 8 in the operational position 22 of the magnetic probe member 5 when there are no printed circuit boards 4 and 25. It is also made of sections. The measuring winding 9 comprises the sections 29 and 30 analogous to the sections 27 and 28 of the measuring winding 8 and positioned symmetrically to each other in relation to the exciting winding 7 and the magnetic probe member 5. To increase the level of voltage balance between the measuring windings 8 and 9 in the absense of the test printed circuit board 4 and the sample board 25, the distance between the exciting winding 7 and the measuring windings 8 and 9 exceeds 4-5 radii of the exciting winding 7, whereas the distance between the measuring windings 8 and 9 and the ends 32 and 33 of the magnetic probe member 5 exceeds 10 radii of the magnetic probe member 5.

In case in the process of testing it is required to determine deviations of parameters of the electrically conductive plating 2 from the nominal ones, it is advisable to make the measurements with the help of the sample printed circuit board 25 placed into the gap 24 (FIG. 5).

Increased "useful signal/interference" ratio, in the embodiments of the eddy current sensor 1 of FIGS. 4 and 5 with varying parameters of the termination pads 26 of the test holes, can be accounted for in the following way. Eddy currents circulating in the plating 2 and in the termination pads 26 cause an increased leakage flux. It becomes difficult to separate the effect of varying parameters of the termination pad 26 and the electrically conductive plating 2 by measuring variations of the main flux 34 (FIG. 6). At the same time, the leakage flux 35, which is determined by the effect of the termination pads 26, is "pushed away" farther from the magnetic probe member 5 than the leakage magnetic flux 36 caused by the effects of the parameters of the electrically conductive plating 2. After measurements done in the operational position 22 of the magnetic probe member 5, the current in the solenoid 13 is cut off and the magnetic probe member 5 assumes its initial position 21. The test printed circuit board 4 is shifted and parameters of the electrically conductive plating in the next hole are measured. To install or replace the sample printed circuit board 25, the screw 20 is removed and the magnetic probe member is moved aside.

Because the sections 27 and 28 of the measuring winding 8 and the sections 29 and 30 of the measuring winding 9 are positioned so that their projections lie within the limits of respective termination pads 26, exclusion of the effects of the leakage flux 35 is permitted.

We claim:

1. An eddy current sensor for non-destructive testing of quality of electrically conductive through-hole plating in printed circuit boards comprising:
    an elongated magnetic probe member having a first end and a second end, said probe member being movable and insertable into said through-plated hole of said printed circuit board when the latter is positioned in the path of movement;
    means for moving said magnetic probe member for inserting said magnetic probe member into said hole of said printed circuit board;
    a first winding coaxial with the probe's path of movement for inducing eddy currents in said electrically conductive plating of printed circuit boards holes when the latter are positioned adjacent thereto;
    a second winding coaxial with the probe's path of movement and magnetically coupled with and rigidly fixed with respect to said first winding and positioned at a predetermined distance from said first winding for forming a gap to insert said tested printed circuit board;
    a third winding coaxial with the probe's path of movement, connected in opposition to said second winding and magnetically coupled with the first winding, said third winding being rigidly fixed with respect to said first winding and said second winding and being positioned at a predetermined distance from said first winding on the other side in relation to said second winding, said first winding comprising an exciting winding, said second and third windings comprising measuring windings located on opposite sides of said first winding, said measuring windings being rigidly fixed relative to said exciting winding and said probe, when moved, being positioned axially within said windings and said through holes.

2. An eddy current sensor as claimed in claim 1, wherein the means for moving the magnetic probe member comprises an electromagnetic drive.

3. An eddy current sensor as claimed in claim 2, wherein the electromagnetic drive comprises:
    a solenoid;
    a magnetized screw coaxially placed in said solenoid;
    a spring on said magnetized screw;
    a ferromagnetic core having a first tip and a second tip and coaxially mounted in said solenoid, said first tip being connected to said spring, the core being movable along the axis of said solenoid;
    a dielectric rod having a first tip and a second tip and being connected by its first tip to said second tip of said ferromagnetic core, the second tip of said dielectric rod being connected to said magnetic probe member.

4. An eddy current sensor as claimed in claim 3, comprising:
    said second winding being separated from said first winding by a distance of more than 4 radii of said first winding, said second winding being separated from said first end of said magnetic probe member by a distance of more than 10 radii of said magnetic probe member when the latter is inserted therein during a test for reducing interferences caused by possible variations of the distance between the second winding and the first end of the magnetic probe member and the first winding;
    said third winding being separated from said first winding by a distance of more than 4 radii of said first winding and being separated from said second end of said magnetic probe member by a distance of more than 10 radii of said magnetic probe member when the latter is inserted therein during a test for reducing interference caused by possible variations of the distance between the third winding and the second end of the magnetic probe member and the first winding.

5. An eddy current sensor for non-destructive testing of quality of electrically conductive through-hole plating in printed circuit boards having termination pads comprising:

an elongated magnetic probe member with a first end and a second end movable into a hole of said printed circuit board when the latter is positioned in the path of movement;

means for moving said magnetic probe member for inserting said magnetic probe member into said hole of said printed circuit board;

a first winding coaxial with said magnetic probe member for inducing eddy currents in electrically conductive through-hole plating of printed circuit boards when the latter are positioned adjacent thereto;

a second winding coaxial with the probe's path of movement and magnetically coupled with and rigidly fixed with respect to said first winding and positioned at a predetermined distance from said first winding for forming a gap for said test printed circuit board to be inserted;

a plurality of coaxial coplanar sections of said second winding in aiding connection between each other and positioned at a predetermined radial distance from said magnetic probe member symmetrically to its axis, said sections projecting radially within limits of corresponding termination pads of said through-plated hole in said test printed circuit board;

a third winding coaxial with the probe's path of movement and connected in opposition to said second winding and magnetically coupled with said first winding, said third winding being rigidly fixed with respect to said first winding and said second winding and being positioned at a predetermined distance from said first winding on the other side in relation to said second winding with a gap provided for insertion of an additional printed circuit board;

said third winding having a plurality of coaxial coplanar sections in aiding connection and positioned at a predetermined radial distance from said magnetic probe member symmetrically about its axis, said sections of said third winding projecting radially within limits of respective termination pads of said through-plated holes of the additional printed circuit board, said first winding comprising an exciting winding, said second and third windings comprising measuring windings located on opposite sides of said first winding, said measuring windings being rigidly fixed relative to said exciting winding and said probe, when moved, being positioned within said windings and said through holes.

* * * * *